United States Patent
Weckbecker et al.

[11] Patent Number: 5,856,495
[45] Date of Patent: Jan. 5, 1999

[54] PROCESS FOR THE PREPARATION OF TRIAZOLINONE HERBICIDES

[75] Inventors: Christoph Weckbecker, Hanau; Karlboing Drauz, Freigericht, both of Germany

[73] Assignee: Degussa Aktiengesellschaft, Frankfurt, Germany

[21] Appl. No.: 785,830

[22] Filed: Jan. 15, 1997

[30] Foreign Application Priority Data

Jan. 15, 1996 [DE] Germany ............... 196 01 190.6

[51] Int. Cl.$^6$ ............... C07D 249/12; C07D 471/04
[52] U.S. Cl. ............... 546/272.4; 548/263.2
[58] Field of Search ............... 548/263.2; 546/272.4

[56] References Cited

U.S. PATENT DOCUMENTS

| | | | |
|---|---|---|---|
| 3,080,358 | 3/1963 | Ottenheyn et al. | 71/92 |
| 4,139,364 | 2/1979 | Wolf | 71/92 |
| 4,818,276 | 4/1989 | Maravetz et al. | 71/92 |

FOREIGN PATENT DOCUMENTS

| | | |
|---|---|---|
| 220 952 | 5/1987 | European Pat. Off. . |
| 270 061 | 6/1988 | European Pat. Off. . |
| 317 947 | 5/1989 | European Pat. Off. . |
| 28 01 429 | 7/1978 | Germany . |
| 2 056 971 | 3/1981 | United Kingdom . |
| 2 090 250 | 12/1981 | United Kingdom . |
| 94/22828 | 10/1994 | WIPO . |

OTHER PUBLICATIONS

Temple, "Triazoles 1, 2, 4" 1981, pp. 365–385, 404–421, 443–461 and 516–521.

*Primary Examiner*—Zinna Northington Davis
*Attorney, Agent, or Firm*—Cushman Darby & Cushman IP Group of Pillsbury Madison & Sutro, LLP

[57] ABSTRACT

A process for the preparation of substituted 1,2,4-triazoline-3(2H)-ones of general formula (I)

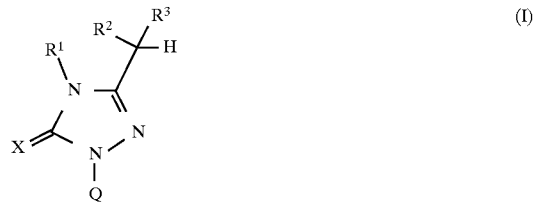

by reacting an amide of general formula (IV)

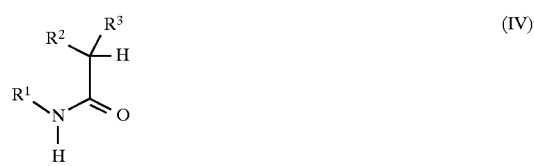

with phosgen or thiophosgen or a phosgen substitute or thiophosgen substitute to a compound of general formula V

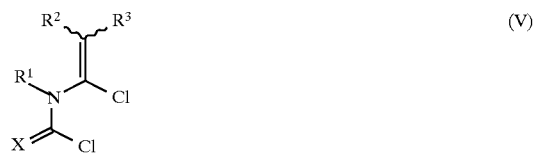

and subsequent reaction of (V) with a compound of general formula (VI) or of an acid addition salt of (VI)

$$Q\text{—}NH\text{—}NH\text{—}CO\text{—}R^{26} \quad (VI)$$

to compounds of general formula (I).

Compounds of general formula (I) can be used as herbicides.

17 Claims, No Drawings

PROCESS FOR THE PREPARATION OF TRIAZOLINONE HERBICIDES

BACKGROUND OF THE INVENTION

1. Field of Invention

The invention relates to a novel process for the preparation of 1,2,4-triazoline-3(2H)-ones, hereinafter also referred to in simplified form as triazolinones, a class of compound of general formula (I),

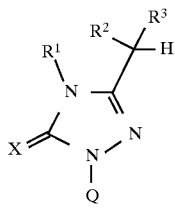

(I)

where

X=O or S, $R^1$=($C_2$–$C_8$) alkoxyalkyl, ($C_2$–$C_8$) haloalkoxyalkyl, ($C_1$–$C_8$) alkyl, ($C_1$–$C_8$) haloalkyl, ($C_1$–$C_8$) cyanoalkyl, ($C_2$–$C_8$) alkylthioalkyl, ($C_2$–$C_8$) alkylsulfinylalkyl, ($C_2$–$C_8$) alkylsulfonylalkyl, ($C_7$–$C_8$) arylalkyl for example benzyl, ($C_2$–$C_8$) alkenyl, ($C_2$–$C_8$) haloalkenyl, ($C_2$–$C_8$) alkinyl, ($C_2$–$C_8$) haloalkinyl, aryl for example naphthyl or phenyl, that may be substituted once or many times with halogen, ($C_1$–$C_3$) alkyl or ($C_1$–$C_3$) alkoxy, heteroaryl for example pyridine, where heteroaryl may optionally be substituted by halogen, $R^2$ and $R^3$, independently of one another represent, H, ($C_2$–$C_6$) alkoxyalkyl, ($C_2$–$C_6$) haloalkoxyalkyl, ($C_1$–$C_6$) alkyl, ($C_1$–$C_6$) haloalkyl, ($C_1$–$C_6$) cyanoalkyl, ($C_1$–$C_6$) alkylthio, ($C_2$–$C_6$) alkylthioalkyl, ($C_2$–$C_6$) alkylsulfinylalkyl, ($C_2$–$C_6$) alkylsulfonylalkyl, ($C_7$–$C_8$) arylalkyl for example benzyl, ($C_2$–$C_6$) alkenyl, ($C_2$–$C_6$) haloalkenyl, ($C_2$–$C_6$) alkinyl, ($C_2$–$C_6$) haloalkinyl; aryl for example naphthyl or phenyl, that may be substituted once or many times with halogen, ($C_1$–$C_3$) alkyl or ($C_1$–$C_3$) alkoxy, heteroaryl for example pyridine, where $R^1$ and $R^2$ may also be associated to form a ring to produce structure (II),

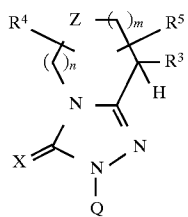

(II)

where n and m independently of one another are 0, 1, 2 or 3,

Z=$CR^4R^5$, O, S, S(O), S(O)$_2$, N(($C_1$–$C_4$)alkyl), N(($C_1$–$C_4$)haloalkyl), C=O, C=N—$R^4$ or C=S, $R^4$=H, ($C_1$–$C_3$) alkyl, halogen, ($C_1$–$C_6$) alkoxy, ($C_1$–$C_6$) haloalkyl, ($C_1$–$C_6$) haloalkoxy, ($C_2$–$C_6$) alkylcarbonyloxy or ($C_2$–$C_6$) haloalkylcarbonyloxy, $R^5$=H, ($C_1$–$C_3$) alkyl or halogen, where $R^4$ and $R^5$, independently of one another, can substitute the ring once or many times and occupy up to 12 (m=3, n=3) positions, Q stands for one of the radicals

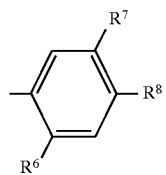  Q-1

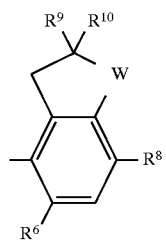  Q-2

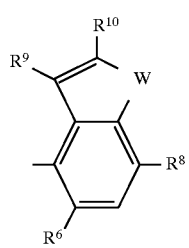  Q-3

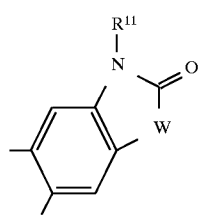  Q-4

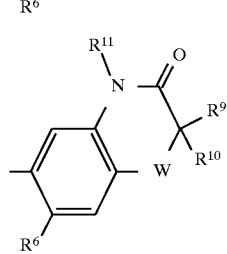  Q-5

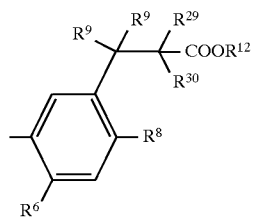  Q-6

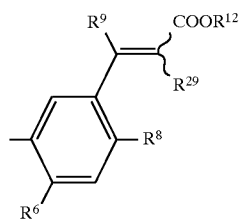  Q-7 where

W=O or S, $R^6$=H, halogen, $R^7$=H, $(C_1-C_8)$ alkyl, $(C_1-C_8)$ haloalkyl, halogen, OH, $OR^{12}$, SH, $S(O)_pR^{12}$, $COR^{12}$, $CO_2R^{12}$, $C(O)SR^{12}$, $C(O)NR^{14}R^{15}$, CHO, $CR^{14}$=$NOR^{21}$, $CHCR^{22}CO_2R^{12}$, $CH_2CHR^{22}CO_2R^{12}$, $CO_2N$=$CR^{16}R^{17}$, $NO_2$, CN, $NHSO_2R^{18}$, $NHSO_2NHR^{18}$, $NR^{12}R^{23}$, $NH_2$ or phenyl, optionally substituted by $R^{24}$, p=0,1 or 2, $R^8$=$(C_1-C_2)$ alkyl, $(C_1-C_2)$ haloalkyl, $OCH_3$, $SCH_3$, $OCHF_2$, halogen, CN or $NO_2$, $R^9$=H, $(C1-C_3)$ alkyl or halogen, $R^{10}$=H, $(C_1-C_3)$ alkyl, halogen, $(C_1-C_3)$ haloalkyl, cyclopropyl, Vinyl, $C_2-C_8$-alkinyl, CN, $C(O)R^{23}$,$CO_2R^{23}$, $C(O)NR^{23}R^{25}$, $CR^{19}R^{20}CN$, $CR^{19}R^{20}C(O)R^{23}$, $CR^{19}R^{20}CO_2R^{23}$, $CR^{19}R^{20}C(O)NR^{23}R^{25}$, $CHR^{19}OH$, $CHR^{19}OC(O)R^{23}$ or $OCHR^{19}OC(O)NR^{23}R^{25}$, or, when Q equals Q-2, $R^9$ and $R^{10}$ can together with the carbon atom to which they are bound be C=O, $R^{11}$=H, $(C_1-C_6)$ alkyl, $(C_1-C_6)$ haloalkyl, $(C_3-C_6)$ haloalkenyl, $(C_2-C_6)$ alkoxyalkyl, $(C_3-C_6)$ alkenyl, $(C_3-C_6)$ alkinyl, $(C_3-C_6)$ haloalkinyl, $(C_4-C_7)$ cycloalkylalkyl,

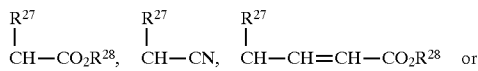

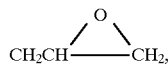

$R^{12}$=$(C_1-C_8)$ alkyl, $(C_3-C_8)$ cycloalkyl, $(C_3-C_8)$ alkenyl, $(C_3-C_8)$ alkinyl, $(C_1-C_8)$ haloalkyl, $(C_2-C_8)$ alkoxyalkyl, $(C_2-C_8)$ alkylthioalkyl, $(C_2-C_8)$ alkylsulfinylalkyl, $(C_2-C_8)$ alkylsulfonylalkyl, $(C_4-C_8)$ alkoxyalkoxyalkyl, $(C_4-C_8)$ cycloalkylalkyl, $(C_6-C_8)$ cycloalkoxyalkyl, $(C_4-C_8)$ alkenyloxyalkyl, $(C_4-C_8)$ alkinyloxyalkyl, $(C_3-C_8)$ haloalkoxyalkyl, $(C_4-C_8)$ haloalkenyloxyalkyl, $(C_4-C_8)$ haloalkinyloxyalkyl, $(C_6-C_8)$ cycloalkylthioalkyl, $(C_4-C_8)$ alkenylthioalkyl, $(C_4-C_8)$ alkinylthioalkyl, $(C_1-C_4)$ alkyl, substituted by phenoxy or benzyloxy, each ring optionally substituted by halogen, $(C_1-C_3)$ alkyl or $(C_1-C_3)$ haloalkyl, $(C_4-C_8)$ trialkylsilylalkyl, $(C_3-C_8)$ cyanoalkyl, $(C_3-C_8)$ halocycloalkyl, $(C_3-C_8)$ haloalkenyl, $(C_5-C_8)$ alkoxyalkenyl, $(C_5-C_8)$ haloalkoxyalkenyl, $(C_5-C_8)$ alkylthioalkenyl, $(C_3-C_8)$ haloalkinyl, $(C_5-C_8)$ alkoxyalkinyl, $(C_5-C_8)$ haloalkoxyalkinyl, $(C_5-C_8)$ alkylthioalkinyl, $(C_2-C_8)$ alkylcarbonyl, benzyl, optionally substituted by halogen, $(C_1-C_3)$ alkyl or $(C_1-C_3)$ haloalkyl, $CHR^{19}COR^{13}$, $CHR^{19}P(O)(OR^{13})$ $CHR^{19}P(S)$ $(OR^{13})_2$, $P(O) (OR^{13})_2$, $P(S)(OR^{13})_2$, $CHR^{19}C(O)NR^{14}R^{15}$, $CHR^{19}C(O)NH_2$, $CHR^{19}CO_2R^{13}$, $CO_2R^{13}$, $SO_2R^{13}$, phenyl, optionally substituted by $R^{24}$,

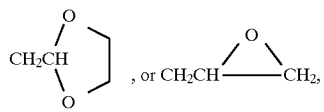

$R^{13}$=$(C_1-C_6)$ alkyl, $(C_1-C_6)$ haloalkyl, $(C_3-C_6)$ alkenyl or $(C_3-C_6)$ alkinyl, $R^{14}$ and $R^{16}$=independently of one another, H or $(C_1-C_4)$ alkyl, $R^{15}$ and $R^{17}$=independently of one another, $(C_1-C_4)$ alkyl or phenyl, optionally substituted by halogen, $(C_1-C_3)$ alkyl or $(C_1-C_3)$ haloalkyl, $R^{14}$ and $R^{15}$ can, together with the nitrogen atom that binds them, form a piperidinyl-, pyrrolidinyl- or morpholinyl-ring, each ring optionally substituted by $(C_1-C_3)$ alkyl, phenyl or benzyl, or $R^{16}$ and $R^{17}$ can, together with the carbon atom that binds them, be $(C_3-C_8)$ cycloalkyl, $R^{18}$=$(C_1-C_4)$ alkyl or $(C_1-C_4)$ haloalkyl, $R^{19}$ and $R^{20}$=independently H or $(C_1-C_5)$ alkyl, $R^{21}$H, $(C_1-C_6)$ alkyl, $(C_3-C_6)$ alkenyl or $(C_3-C_6)$ alkinyl, $R^{22}$ and $R^{27}$=independently of one another, H, $(C_1-C_4)$ alkyl or halogen, or $R^{12}$ and $R^{22}$ can together form a $(C_2-C_3)$ alkylen, $R^{23}$, $R^{24}$ and $R^{28}$=independently of one another, H or $(C_1-C_4)$ alkyl, $R^{25}$=$(C_1-C_2)$ alkyl, $(C_1-C_2)$ haloalkyl, $OCH_3$, $SCH_3$, $OCHF_2$, halogen, CN or $NO_2$ and $R^{26}$=H, $(C_1-C_5)$ alkyl, $(C_1-C_5)$ haloalkyl, $(C_3-C_6)$ cycloalkyl, $(C_3-C_6)$ halocycloalkyl, $(C_1-C_5)$ alkoxy, $(C_1-C_5)$ haloalkoxy and phenyl, that may optionally be substituted up to three times optionally by halogen, $NO_2$, cyano, $(C_1-C_2)$ alkyl, $(C_1-C_2)$ haloalkyl, $(C_1-C_2)$ alkoxy or $(C_1-C_2)$ haloalkoxy, $R^{29}$=H, halogen or $(C_1-C_6)$ alkyl, $R^{30}$=H, $(C_1-C_4)$ alkyl or halogen.

The compounds of formulae I or II are highly active herbicides, which act as protoporphyrinogen oxidase inhibitor and control unwanted grasses and weeds, even when used in small amounts. I and II are, for example, of great interest for cultures with plantations where fast-growing and robust destructive plants impair the harvest. Thanks to the excellent selectivity of type I or II, these compounds can, however, also be used in cultivated plants, for example maize, soya, wheat or barley to combat destructive plants.

2. Related Art

Known processes for the preparation of compound I generally start with an appropriately substituted phenylhydrazine which is converted into the corresponding triazolidinone by reaction with an N-(1-alkoxy)alkylidene alkylcarbamate or with an α-ketocarboxylic acid derivative and by subsequent Schmidt rearrangement into the corresponding triazolidinones.

EP 0 220 952 for example describes the conversion carried out in xylene of 2-chlorophenyl hydrazine with N-(1-ethoxy)ethylidene ethylcarbamate into triazolinone unsubstituted in 4-position which is then alkylated in an independent reaction step in dimethylformamide into the tri-substituted triazolinone. It is very laborious to prepare bicyclic triazolinones in this manner.

U.S. Pat. No. 4,818,275 and U.S. Pat. No. 4,818,276 also describe processes for substituted triazolinones. Acid condensation of the phenyl hydrazine used with an a-ketocarboxylic acid first yields the hydrazone which undergoes Schmidt rearrangement by reaction with diphenyl phosphorylazide and is hereby converted into triazolinone. The triazolinone formed also has to be alkylated into the final compound in a subsequent reaction step. It is also very laborious to synthesise bicyclic triazolinones in this manner and the azide used causes problems of technical safety when the compounds are synthesised on an industrial scale.

In other known processes for the preparation of individual representatives of compound type II the reaction generally occurs via the corresponding amidrazone which is reacted to bicyclic compounds.

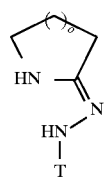

(III)

DE 28 01 429 describes a process for the preparation of compounds of type II in which it is necessary to react 2-piperidone, that first has to be suitably activated using methods known from the literature (see Houben-Weyl, "Methoden der organischen Chemie", Vol. 11/2, p. 578; and DE-OS 19 12 739 and DE-OS 19 12 737) with the HCl-salt of the correspondingly substituted phenylhydrazine to amidrazone (III) (see DT-OS 22 35 177) and cyclisises the amidrazone formed with chloroformic acid methyl ester or phosgen into THF with addition of base to compounds of type II.

In another process (see PCT/WO 94/22828) N-carboxymethyl-2-iminopiperidine hydrochloride is described as activated intermediate compound. The hydrolysis-sensitive intermediate compound is coupled with the correspondingly substituted phenylhydrazine and then cyclisised by acid catalysis to form triazolinone.

The process according to EP 0 317 947 A2 for the synthesis of triazolinones includes the reaction of N-carboxyalkyl lactams with a phenylhydrazine to amidrazone by boiling under reflux in xylene. The bicyclic triazolinone is formed by reaction with phosgen. A disadvantage of the process is that the condensation step to amidrazone only produces a yield of 21 % in the presence of $P_4O_{10}$ as dessicating agent.

The known processes have the disadvantages that they can, in part, only be realised via long synthesis routes which in part lead via intermediate steps that are laborious to produce and to treat, that they supply moderate yields and in part use costly and not always innocuous starting substances and that various by-products are formed which necessitate laborious purification steps.

SUMMARY OF THE INVENTION

It is therefore an object of the invention to provide a process which is devoid of the above disadvantages and which is economically more interesting.

This object for the preparation of compounds of type (I),

where

X=O or S, $R^1$=($C_2$–$C_8$) alkoxyalkyl, ($C_2$–$C_8$) haloalkoxyalkyl, ($C_1$–$C_8$) alkyl, ($C_1$–$C_8$) haloalkyl, ($C_1$–$C_8$) cyanoalkyl, ($C_2$–$C_8$) alkylthioalkyl, ($C_2$–$C_8$) alkylsulfinylalkyl, ($C_2$–$C_8$) alkylsulfonylalkyl, ($C_7$–$C_8$) arylalkyl for example benzyl, ($C_2$–$C_8$) alkenyl, ($C_2$–$C_8$) haloalkenyl, ($C_2$–$C_8$) alkinyl, ($C_2$–$C_8$) haloalkinyl, aryl for example naphthyl or phenyl, that may be substituted once or many times with halogen, ($C_1$–$C_3$) alkyl or ($C_1$–$C_3$) alkoxy, heteroaryl for example pyridine, where heteroaryl may optionally be substituted by halogen, $R^2$ and $R^3$, independently of one another represent, H, ($C_2$–$C_6$) alkoxyalkyl, ($C_2$–$C_6$) haloalkoxyalkyl, ($C_1$–$C_6$) alkyl, ($C_1$–$C_6$) haloalkyl, ($C_1$–$C_6$) cyanoalkyl, ($C_1$–$C_6$) alkylthio, ($C_2$–$C_6$) alkylthioalkyl, ($C_2$–$C_6$) alkylsulfinylalkyl, ($C_2$–$C_6$) alkylsulfonylalkyl, ($C_7$–$C_8$) arylalkyl for example benzyl, ($C_2$–$C_6$) alkenyl, ($C_2$–$C_6$) haloalkenyl, ($C_2$–$C_6$) alkinyl, ($C_2$–$C_6$) haloalkinyl, aryl for example naphthyl or phenyl, that may be substituted once or many times with halogen, ($C_1$–$C_3$) alkyl or ($C_1$–$C_3$) alkoxy, heteroaryl for example pyridine, where $R^1$ and $R^2$ may also be associated to form a ring to produce structure (II),

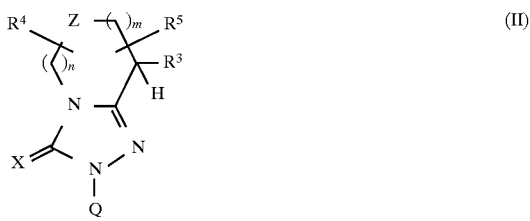

where n and m independently of one another are 0, 1, 2 or 3,

Z=$CR^4R^5$, O, S, S(O), S(O)$_2$, N(($C_1$–$C_4$)alkyl), N(($C_1$–$C_4$)haloalkyl), C=O, C=N—$R^4$ or C=S, $R^4$=H, ($C_1$–$C_3$) alkyl, halogen, ($C_1$–$C_6$) alkoxy, ($C_1$–$C_6$) haloalkyl, ($C_1$–$C_6$) haloalkoxy, ($C_2$–$C_6$) alkylcarbonyloxy or ($C_2$–$C_6$) haloalkylcarbonyloxy, $R^5$=H, ($C_1$–$C_3$) alkyl or halogen, where $R^4$ and $R^5$, independently of one another, can substitute the ring once or many times and occupy up to 12 (m=3, n=3) positions, Q stands for one of the radicals

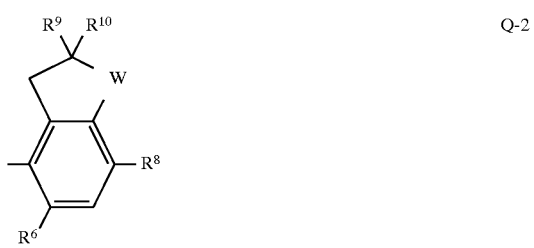

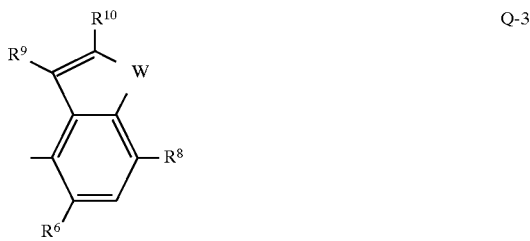

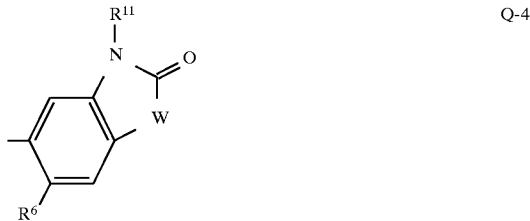

-continued

Q-5

$$\text{[structure with } R^{11}, \text{N}, \text{O}, R^9, R^{10}, W, R^6 \text{]}$$

Q-6

$$\text{[structure with } R^9, R^{29}, \text{COOR}^{12}, R^{30}, R^8, R^6 \text{]}$$

Q-7

$$\text{[structure with } R^9, \text{COOR}^{12}, R^{29}, R^8, R^6 \text{]}$$

where

W=O or S,

R=H, halogen,

R=H, $(C_1-C_8)$ alkyl, $(C_1-C_8)$ haloalkyl, halogen, OH, $OR^{12}$, SH, $S(O)_pR^{12}$, $COR^{12}$, $CO_2R^{12}$, $C(O)SR^{12}$, $C(O)NR^{14}R^{15}$, CHO, $CR^{14}$=$NOR^{21}$, $CHCR^{22}CO_2R^{12}$, $CH_2CHR^{22}CO_2R^{12}$, $CO_2N$=$CR^{16}R^{17}$, $NO_2$, CN, $NHSO_2R^{18}$, $NHSO_2NHR^{18}$, $NR^{12}R^{23}$, $NH_2$ or phenyl, optionally substituted by $R^{24}$, p=0,1 or 2, $R^8$=$(C_1-C_2)$ alkyl, $(C_1-C_2)$ haloalkyl, $OCH_3$, $SCH_3$, $OCHF_2$, halogen, CN or $NO_2$, $R^9$=H, $(C_1-C_3)$ alkyl or halogen, $R^{10}$=H, $(C_1-C_3)$ alkyl, halogen, $(C_1-C_3)$ haloalkyl, cyclopropyl, Vinyl, $C_2$-alkinyl, CN, $C(O)R^{23}$, $CO_2R^{23}$, $C(O)NR^{23}R^{25}$, $CR^{19}R^{20}CN$, $CR^{19}R^{20}C(O)R^{23}$, $CR^{19}R^{20}CO_2R^{23}$, $CR^{19}R^{20}C(O)NR^{23}R^{25}$, $CHR^{19}OH$, $CHR^{19}OC(O)R^{23}$ or $OCHR^{19}OC(O)NR^{23}R^{25}$, or, when Q equals Q-2, $R^9$ and $R^{10}$ can together with the carbon atom to which they are bound be C=O, $R^{11}$=H, $(C_1-C_6)$ alkyl, $(C_1-C_6)$ haloalkyl, $(C_3-C_6)$ haloalkenyl, $(C_2-C_6)$ alkoxyalkyl, $(C_3-C_6)$ alkenyl, $(C_3-C_6)$ alkinyl, $(C_3-C_6)$ haloalkinyl, $(C_4-C_7)$ cycloalkylalkyl, $$\overset{R^{27}}{\underset{|}{CH}}-CO_2R^{28}, \quad \overset{R^{27}}{\underset{|}{CH}}-CN, \quad \overset{R^{27}}{\underset{|}{CH}}-CH=CH-CO_2R^{28} \text{ or}$$

$$CH_2CH\overset{O}{\underset{}{\triangle}}CH_2,$$

$R^{12}$=$(C_1-C_8)$ alkyl, $(C_3-C_8)$ cycloalkyl, $(C_3-C_8)$ alkenyl, $(C_3-C_8)$ alkinyl, $(C_1-C_8)$ haloalkyl, $(C_2-C_8)$ alkoxyalkyl, $(C_2-C_8)$ alkylthioalkyl, $(C_2-C_8)$ alkylsulfinylalkyl, $(C_2-C_8)$ alkylsulfonylalkyl, $(C_4-C_8)$ alkoxyalkoxyalkyl, $(C_4-C_8)$ cycloalkylalkyl, $(C_6-C_8)$ cycloalkoxyalkyl, $(C_4-C_8)$ alkenyloxyalkyl, $(C_4-C_8)$ alkinyloxyalkyl, $(C_3-C_8)$ haloalkoxyalkyl, $(C_4-C_8)$ haloalkenyloxyalkyl, $(C_4-C_8)$ haloalkinyloxyalkyl, $(C_6-C_8)$ cycloalkylthioalkyl, $(C_4-C_8)$ alkenylthioalkyl, $(C_4-C_8)$ alkinylthioalkyl, $(C_1-C_4)$ alkyl, substituted by phenoxy or benzyloxy, each ring optionally substituted by halogen, $(C_1-C_3)$ alkyl or $(C_1-C_3)$ haloalkyl, $(C_4-C_8)$ trialkylsilylalkyl, $(C_3-C_8)$ cyanoalkyl, $(C_3-C_8)$ halocycloalkyl, $(C_3-C_8)$ haloalkenyl, $(C_5-C_8)$ alkoxyalkenyl, $(C_5-C_8)$ haloalkoxyalkenyl, $(C_5-C_8)$ alkylthioalkenyl, $(C_3-C_8)$ haloalkinyl, $(C_5-C_8)$ alkoxyalkinyl, $(C_5-C_8)$ haloalkoxyalkinyl, $(C_5-C_8)$ alkylthioalkinyl, $(C_2-C_8)$ alkylcarbonyl, benzyl, optionally substituted by halogen, $(C_1-C_3)$ alkyl or $(C_1-C_3)$ haloalkyl, $CHR^{19}COR^{13}$, $CHR^{19}P(O)(OR^{13})_2$, $CHR^{19}P(S)$ $(OR^{13})_2$, $P(O)(OR^{13})_2$, $P(S)(OR^{13})_2$, $CHR^{19}C(O)NR^{14}R^{15}$, $CHR^{19}C(O)NH_2$, $CHR^{19}CO_2R^{13}$, $CO_2R^{13}$, $SO_2R^{13}$, phenyl, optionally substituted by $R^{24}$, $$CH_2CH\overset{O}{\underset{O}{\diagdown}} , \text{ or } CH_2CH\overset{O}{\underset{}{\triangle}}CH_2,$$

$R^{13}$=$(C_1-C_6)$ alkyl, $(C_1-C_6)$ haloalkyl, $(C_3-C_6)$ alkenyl or $(C_3-C_6)$ alkinyl, $R^{14}$ and $R^{16}$=independently of one another, H or $(C_1-C_4)$ alkyl, $R^{15}$ and $R^{17}$=independently of one another, $(C_1-C_4)$ alkyl or phenyl, optionally substituted by halogen, $(C_1-C_3)$ alkyl or $(C_1-C_3)$ haloalkyl, or $R^{14}$ and $R^{15}$ can, together with the nitrogen atom that binds them, form a piperidinyl-, pyrrolidinyl- or morpholinyl-ring, each ring optionally substituted by $(C_1-C_3)$ alkyl, phenyl or benzyl, or $R^{16}$ and $R^{17}$ can, together with the carbon atom that binds them, be $(C_3-C_8)$ cycloalkyl, $R^{18}$=$(C_1-C_4)$ alkyl or $(C_1-C_4)$ haloalkyl, $R^{19}$ and $R^{20}$=independently H or $(C_1-C_5)$ alkyl, $R^{21}$=H, $(C_1-C_6)$ alkyl, $(C_3-C_6)$ alkenyl or $(C_3-C_6)$ alkinyl, $R^{22}$ and $R^{27}$=independently of one another, H, $(C_1-C_4)$ alkyl or halogen, or $R^{12}$ and $R^{22}$ can together form a $(C_2-C_3)$ alkylen, $R^{23}$, $R^{24}$ and $R^{28}$=independently of one another, H or $(C_1-C_4)$ alkyl, $R^{25}$=$(C_1-C_2)$ alkyl, $(C_1-C_2)$ haloalkyl, $OCH_3$, $SCH_3$, $OCHF_2$, halogen, CN or $NO_2$ and $R^{26}$=H, $(C_1-C_5)$ alkyl, $(C_1-C_5)$ haloalkyl, $(C_3-C_6)$ cycloalkyl, $(C_3-C_6)$ halocycloalkyl, $(C_1-C_5)$ alkoxy, $(C_1-C_5)$ haloalkoxy and phenyl, that may optionally be substituted up to three times optionally by halogen, $NO_2$, cyano, $(C_1-C_2)$ alkyl, $(C_1-C_2)$ haloalkyl, $(C_1-C_2)$ alkoxy or $(C_1-C_2)$ haloalkoxy, $R^{29}$=H, halogen or $(C_1-C_6)$ alkyl, $R^{30}$=H, $(C_1-C_4)$ alkyl or halogen is solved in the process according to the invention by reacting amides of general formula (IV)

$$\text{[structure IV with } R^2, R^3, R^1, N, H, O, H \text{]} \tag{IV}$$

where $R^1$, $R^2$ and $R^3$ have the meaning given above in a manner known per se with phosgen or thiophosgen or a phosgen substitute or thiophosgen substitute optionally in a solvent to a compound of formula (V)

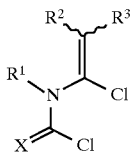

(V)

where $R^1$, $R^2$, $R^3$ and X have the meaning given above and these compounds of formula (V) are subsequently reacted with a compound of formula (VI) or an acid addition salt thereof,

(VI)

where Q and $R^{26}$ have the meaning given above, optionally in the presence of a diluting agent and optionally in the presence of a base and then reacts in the presence of an acid and optionally by increasing the temperature into a compound of formulae (I) or (II).

DETAILED DESCRIPTION OF PREFERRED EMBODIMENTS

It is preferably possible according to the process of the invention to produce compounds of type II

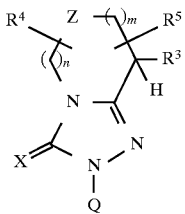

(II)

where
X=O,
n and m independently of one another are 0, 1 or 2,
Z=$CR^4R^5$, O, S, C=O or C=S,
$R^4$=H, ($C_1$–$C_2$) alkyl, ($C_1$–$C_2$) haloalkyl, fluorine, chlorine, ($C_1$–$C_3$) alkoxy or ($C_1$–$C_3$) haloalkoxy,
$R^3$ and $R^5$ can independently of one another be H, ($C_1$–$C_2$) alkyl, fluorine or chlorine,
Q=Q-1, Q-2 or Q-5,
$R^7$H, ($C_1$–$C_8$) alkyl, ($C_1$–$C_8$) haloalkyl, halogen, OH, $OR^{12}$, SH, S(O)$_p$R12, $COR^{12}$, $CO_2R^{12}$, $C(O)SR^{12}$, $C(O)NR^{14}R^{15}$, CHO, CH=CHCO$_2R^{12}$, $CO_2$N=$CR^{16}R^{17}$, $NO_2$, CN, $NHSO_2R^{18}$ or $NHSO_2NHR^{15}$ and
$R^{12}$=($C_1$–$C_4$) alkyl, ($C_3$–$C_4$) alkenyl, ($C_3$–$C_4$) alkinyl, ($C_2$–$C_4$) alkoxyalkyl, ($C_1$–$C_4$) haloalkyl, ($C_3$–$C_4$) haloalkenyl or ($C_3$–$C_4$) haloalkinyl,
$R^{26}$=H, by reacting amides of general formula VII

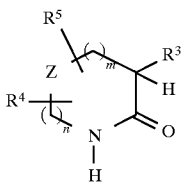

(VII)

where n, m, Z, $R^3$, $R^4$ and $R^5$ have the meaning given above in a manner known per se with phosgen or thiophosgen or a phosgen substitute or thiophosgen substitute optionally in a solvent to a compound of formula VIII

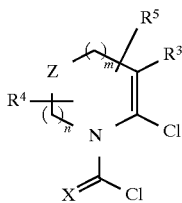

(VIII)

where n, m, X, Z, $R^3$, $R^4$ and $R^5$ have the meaning given above and these compounds of formula (VIII) are then reacted with a compound of formula (VI) or an acid addition salt hereof

(VI)

where Q and $R^{26}$ have the meaning given above optionally in the presence of a diluting agent and optionally first in the presence of a base and then in the presence of an acid and optionally by increasing the temperature to a compound of formula (II).

Quite particularly preferred is a process for the preparation of compounds of type II

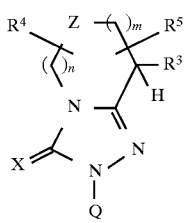

(II)

where
X=O,
n and m independently of one another are 0, 1 or 2,
Z=$CH_2$, CHF, $CF_2$ or CHCl,
$R^4$=H, ($C_1$–$C_2$) alkyl, ($C_1$–$C_2$) haloalkyl, fluorine, chlorine,
$R^5$=H, ($C_1$–$C_2$) alkyl, fluorine, chlorine,
$R^3$=H,
Q=Q-1 or Q-5,
$R^7$=H, ($C_1$–$C_8$) alkyl, ($C_1$–$C_8$) haloalkyl, halogen, OH, $OR^{12}$, SH, S(O)$_p$$R^{12}$, $COR^{12}$, $CO_2R^{12}$, $C(O)SR^{12}$, $C(O)NR^{14}R^{15}$, CHO, CH=CHCO$_2R^{12}$, $CO_2$N=$CR^{16}R^{17}$, $NO_2$, CN, $NHSO_2R^{18}$ or $NHSO_2NHR^{15}$ and
$R^{12}$=($C_1$–$C_4$) alkyl, ($C_3$–$C_4$) alkenyl, ($C_3$–$C_4$) alkinyl, ($C_2$–$C_4$) alkoxyalkyl, ($C_1$–$C_4$) haloalkyl, ($C_3$–$C_4$) haloalkenyl or ($C_3$–$C_4$) haloalkinyl, and
$R^8$=halogen, CN or $NO_2$
$R^{26}$=H by reacting amides of general formula (VII)

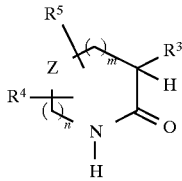

(VII)

where n, m, X, Z, $R^3$, $R^4$ and $R^5$ have the meaning given above in a manner known per se with phosgen or phosgen substitute to compounds of type (VIII)

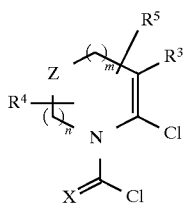

(VIII)

and this compound of type (VIII) is then reacted with a compound of formula (VI) or an acid addition salt thereof

Q—NH—NH—CO—R$^{26}$ (VI)

where Q and R$^{26}$ have the meaning given above optionally in the presence of a diluting agent and optionally in the presence of a base and then reacts in the presence of an acid and optionally by increasing the temperature to a compound of formula (II).

Quite particularly preferred is the process of the invention for the preparation of the compound (IX)

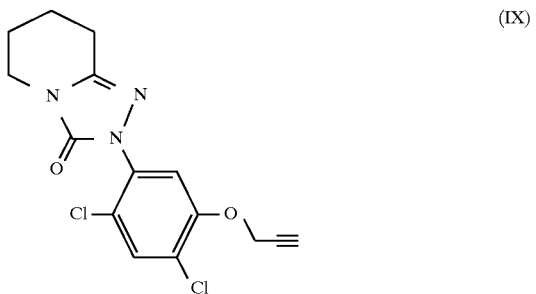

(IX)

by reacting 2-piperidone with phosgen or a phosgen substitute optionally in a solvent in a manner known per se to a compound of formula (X)

(X)

and then allows this compound of formula (X) to react with a compound of formula (XI) or an acid addition salt thereof,

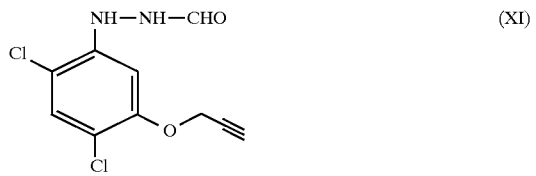

(XI)

optionally in the presence of a diluting agent and optionally in the presence of a base and then in the presence of an acid and optionally with temperature increase into a compound of formula (IX).

The term "alkyl groups" is understood to mean both "straight-chain" and also "branched" alkyl groups. The term "straight-chain alkyl group" is understood for example to mean radicals such as methyl, ethyl, n-propyl, n-butyl, n-pentyl, n-hexyl, "branched alkyl group" radicals such as for example isopropyl or tert.-butyl. "Cycloalkyl" is for example understood to mean radicals such as cyclopropyl, cyclobutyl, cyclopentyl, cyclohexyl or cycloheptyl. The designation halogen stands for fluorine, chlorine, bromine or iodine. The designation "alkoxy group" represents for example methoxy, ethoxy, propoxy, butoxy, isopropoxy, isobutoxy or pentoxy.

Advantageous variants of the process of the invention are protected in the claims dependent on claim 1–4.

A preferred embodiment is a synthesis variant in which the compound of general formula (V)

(V)

can be obtained in high yield in a manner known from the literature according to U.S. Pat. No. 3,080,358 by reacting the amide (IV)

(IV)

with 2–6 mol equivalents of phosgen or thiophosgen or phosgen substitute or thiophosgen substitute in an inert organic solvent, for example in an aromatic solvent such as toluene, chlorobenzene, a halogenated hydrocarbon such as chloroform, methylene chloride, an ether such as diisopropyl ether, tert. butylmethyl ether, tetrahydrofuran or diethyl ether, acetonitrile or carboxylic acid ester, for example acetic acid ethyl ester, acetic acid methyl ester or acetic acid isopropyl ester, at temperatures between −20° C. to +120° C., preferably −20° C. to +70° C. Excess phosgen or thiophosgen is driven out and the solvent optionally drawn off. At 0°–5° C. the compound of formula (V), optionally dissolved in a solvent is added to a solution of the compound of formula (VI) or of an acid addition salt of (VI), such as for example a HCl salt or a H$_2$SO$_4$ salt, in the same solvent or in a different, above cited solvent, optionally in the presence of an acid acceptor, for example an organic base such as triethylamine, tetramethyl piperidine, tributylamine or pyridine or an inorganic base, for example NaOH, KOH, Ca(OH)$_2$, CaO, Na$_2$CO$_3$, K$_2$CO$_3$, CaCO$_3$, NaHCO$_3$, KHCO$_3$ or alkoholates for example NaOCH$_3$ or NaOC$_2$H$_5$, where the compound (XV) is first formed,

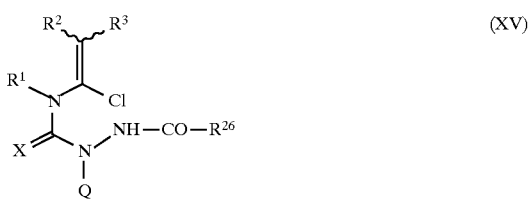

(XV)

which can then be converted optionally in the presence of an organic or inorganic acid, such as for example HCl, H$_2$SO$_4$ HNO$_3$, HCO$_2$H, p-toluene sulfonic acid, acetic acid, camphorsulfonic acid or H$_3$PO$_4$ or an acid ion exchanger and/or by increasing the temperature, for example up to the boiling point of the solvent used, into the compounds of formula (I) or (II). The cyclisation of (XV) to (I) or (II) is advantageously carried out with acid catalysis and/or temperature increase. Secondary reactions may optionally occur without intermediate isolation in the same solvent.

During the reaction to compound (XV) 1–4 molar equivalents of base, particularly preferred 1.5–3.5 molar equivalents of base are advantageously added, where 1 molar equivalent of base serves to release the corresponding acylphenyl hydrazine from the optionally used acylphenyl hydrazine•acid addition salt. Conversion (cyclisation) of compound (XV) into (I) necessitates a certain acid excess. It has been found that the reaction is accelerated more strongly the greater the acid excess. The amount of acid added depends on the previously used amount of base. Particularly preferred acids are $H_2SO_4$ and HCl. A temperature increase, advantageously up to the boiling point of the solvent, accelerates the cyclisation to (I).

In the process according to the invention, the amide unit (IV) is doubly activated in one step via economically very interesting phosgenation or thiophosgenation with the result that a process technology and economically substantially more laborious stepwise activation such as for example according to EP 0 220 952 can be avoided.

Similarly, in the process according to the invention the reaction to (I) occurs in the desired manner starting from (V) and (VI) in one process step, with no need for intermediate working up. This means that compared to known processes, such as for example described in DE 28 01 429, there is a distinct process technology advantage in that coupling, splitting off of the protecting group and cyclisation to the compound of formula (I) can be achieved in just one step.

Using the process described, the reaction can occur in a single pot process and without isolation of intermediate steps, with the result that laborious working up techniques are avoided and the process of the invention permits a smooth course of reaction and by-product formation is extensively avoided and the total yield of (I) is increased. Similarly, the reaction can occur with isolation of the intermediate step (XV).

Amides of general formulae (IV) and (VII) are commercially obtainable or synthesisable after Houben-Weyl, "Methoden der Organischen Chemie", E5, "Carbonsäuren und carbonsäure-Derivate", part 2, p. 934 ff.

The preparation of compound (XI) occurs by formylation of compounds (XII) or (XIII)

(XII)

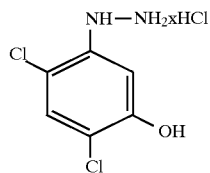

(XIII)

by analogy with current processes known from the literature (see Houben-Weyl, "Methoden der Organ. Chemie", Vol. 15I, p. 165ff; J. March "Advanced Organic Chemistry", 3rd edition, p. 375ff)., where from (XIII) first (XIV)

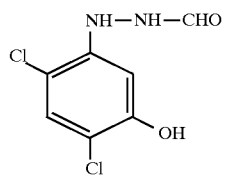

(XIV)

is obtained, that is then etherified according to processes known from the literature(Houben-Weyl, "Methoden der Organ. Chemie", Vol. 6/3 I, p. 49ff and 54ff) to (XI). The compound (XIII) can, in turn, be converted using known etherification reactions (literature reference see above) into (XII), before working continues for example as described with (XII). The compounds(XI) and (XIV) are valuable intermediate compounds for the synthesis of triazolinones and have hitherto not been described in the literature and are therefore new.

The process claimed herein is suitable for the synthesis of bicyclic triazolines of formula (II) with the substitutions cited hereinabove as preferred structures because these structures react particularly easily and clearly or with particularly high yields according to the process to form triazolines. The course of the reaction for the preparation of compounds of general structure (II) is analogous to the preferred embodiment for the preparation of compounds of general formula (I). The intermediate isolation of the corresponding intermediate compounds is not necessary and without further working up the process can be carried out in a reaction vessel without changing the solvent starting from (VI) and (XI) until the corresponding preferred compound of formula (II), toluene, acetonitrile, acetic acid ethyl ester, acetic acid methyl ester, acetic acid isopropyl ester methylene chloride and chloroform being suitable for this reaction. The reaction preferably occurs at temperatures between –20° C. and +70° C. The preferred bases used are organic bases such as triethylamine, tributylamine, pyridine or inorganic bases such as $Na_2CO_3$, $K_2CO_3$, $CaCO_3$. Acids that are preferably used are HCl, $H_2SO_4$, $H_3PO_4$, acetic acid, p-toluene sulfonic acid.

The process claimed is particularly preferred for the synthesis of 2-[2,4-dichloro-5-(2-propynyloxy)phenyl]-5,6, 7,8-tetrahydro-1,2,4-triazolo[4,3-a]pyridine-3(2H)-one of formula IX)

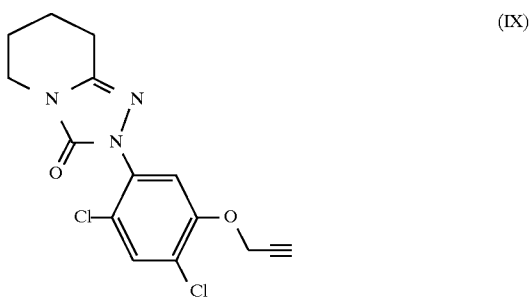

(IX)

in which the compound of formula (X) is obtained by

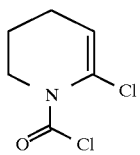

(X)

reacting 2-piperidone with 2–6 molar equivalents of phosgen or phosgen substitute in an inert organic solvent, for example in an aromatic solvent such as toluene, chlorobenzene, a halogenated hydrocarbon such as chloroform, methylene chloride, an ether such as diisopropyl ether, tert. butylmethyl ether, tetrahydrofuran or diethylether, acetonitrile or carboxylic acid esters, for example acetic acid ethyl ester, acetic acid methyl ester or acetic acid isopropyl ester, at temperatures between –20° C. to 120° C., preferably –20° C. to +70° C. in a manner known from the literature according to U.S. Pat. No. 3,080,358 in over 94% yield. Excess phosgen is driven out and the solvent optionally withdrawn. At 0°–5° C. the compound of formula (X) is added, optionally in the same solvent or another above-cited solvent to a solution of the compound of formula (XI) or an acid addition salt of (XI), such as for example an HCL salt or an $H_2SO_4$ salt

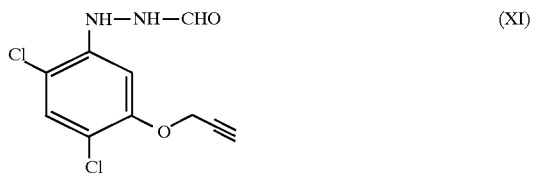

in the same solvent or optionally in a different, above-cited solvent, optionally in the presence of an acid acceptor, for example of an organic base such as triethylamine tetramethyl piperidine, tributylamine or pyridine or of an inorganic base such as NaOH, KOH, $Ca(OH)_2$, CaO, $Na_2CO_3$, $K_2CO_3$, $CaCO_3$, $NaHCO_3$, $KHCO_3$ or alcoholates such as $NaOCH_3$ or $NaOC_2H_5$, where the compound (XVI) is first formed,

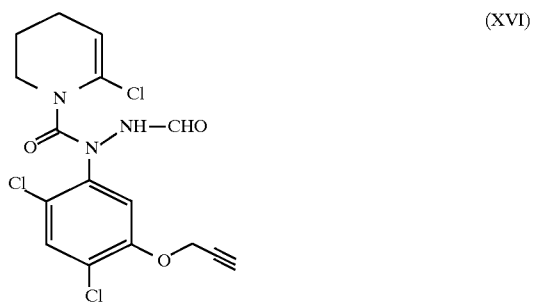

which is then converted optionally in the presence of an organic or inorganic acid such as for example HCl, $H_2SO_4$ $HNO_3$, $HCO_2H$, p-toluene sulfonic acid, acetic acid, camphorsulfonic acid or $H_3PO_4$ or of an acid ion exchanger and/or by increasing the temperature, for example up to the boiling point of the solvent used, into the compound of formula (IX)

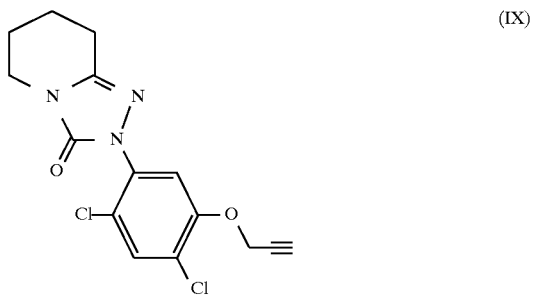

The cyclisation from (XVI) to (IX) is advantageously carried out under acid catalysis and/or temperature increase.

In the reaction to the compound (XVI) 1–4 molar equivalents of base are preferably used, 1.5–3.5 molar equivalents being particularly preferred, where 1 molar equivalent of base serves to liberate the corresponding acylphenylhydrazine from the optionally used acylphenylhydrazine•acid addition salt. A certain acid excess is needed to convert (cyclisation) compound (XVI) into (IX). It has been found that the reaction is accelerated all the more, the greater the acid excess. The amount of added acid depends on the previously used amount of base. Particularly preferred acids are $H_2SO_4$ and HCl. Temperature increase, preferably up to the boiling point of the solvent, accelerates the cyclisation (IX).

In the process of the invention, skilful handling of the reaction doubly activates 2 - piperidone in one step via the economically very interesting phosgenation or thiophosgenation, with the result that it is possible to avoid a stepwise activation, such as for example according to EP 0 220 952, that is considerably more laborious from the point of view of process technology and cost.

In the process according to the invention the reaction to (IX) also occurs starting from (X) and (XI) in one process step in the desired manner without need for intermediate working up. This means that, compared to known processes, such as described for example in DE 28 01 429, a clear process technology advantage arises in that coupling, splitting off of the protecting group and cyclisation to the compound of formula (IX) can be achieved in only one step.

Using the procedure described, the reaction can occur starting from the compounds (X) and (XI) in the single pot process and without isolation of intermediate steps, with the result that laborious working up techniques are avoided and a smooth course of reaction is possible in the process of the invention and the formation of by-products is largely avoided and the total yield of (IX) increased. Similarly, the reaction can occur with isolation of the intermediate step (XVI).

The invention will now be described with reference to the examples, but is not limited hereto.

EXAMPLES

Preparation of 2-[2,4-dichloro-5-(2-propinyloxy)phenyl]-5,6,7,8-tetrahydro-1,2,4-triazolo[4,3-a]pyridine-3(2H)-one and primary step sytheses 1) N-Chlorocarbonyl-2-chloro-1,4,5,6-tetrahydropyridine Diphosgene (25 mmol=15,3 g) is prepared at –10° C. and active charcoal (0.25 g) added to accelerate the formation of phosgen. δ-Valerolactam (25 mmol=2.55 g) dissolved in acetic acid ethyl ester p.a. (20 ml) is added dropwise in 1.5 hours at –10° to 0° C. The mixture is heated to 25° C. until no more δ-valerolactam can be detected in the thin layer chromatogram. The mixture is heated slowly to 50° C., a strong development of gas being detectable. Only one product spot is visible in the thin layer chromatogram. The active charcoal is filtered off and the filtrate concentrated. 4.25 g (=94.4% yield) of the product is isolated as a pale yellow oil.

2) Formic acid N'-(2,4-dichloro-5-hydroxyphenyl)-hydrazide sodium salt 2,4-Dichloro-5-hydroxyphenylhydrazine hydrochloride (11.5 g, 0.05 mol) is added to a solution of 30% methanolic solution of sodium methanolate (22.5 g, 0.125 mol) in methanol at room temperature. A suspension is formed to which methylformiate (62 ml, 1 mol) is added at the same temperature. This mixture is then stirred for 2 hours at 40°–50° C. and then over night at room temperature. The product is filtered off, the filter residue is washed with methanol and the filtrate then concentrated under reduced pressure. The residue is taken up in toluene and during concentration under reduced pressure a pale brown powder is formed that is combined with the above-mentioned filter residue. Yield: 12.5 g (=99%) Melting point: 202°–204° C. (with decomposition)

3) Formic acid N'-(2,4-dichloro-5-(2-propinyloxy)-phenyl)hydrazide

A stirred suspension of formic acid N'-(2,4-dichloro-5-hydroxyphenyl)-hydrazide sodium salt (1.1 g, 5 mmol) in a mixture of 25 ml acetone and 25 ml water is reacted at room temperature with benzene sulfonic acid-(2-propargyl)ester (1.01 g, 5 mmol). Sodium hydroxide solution (0,2 g, 5 mmol in 5 ml water) is added dropwise within 30 minutes so that the pH value lies between 9.5 and 10. The result is reacted with 10 ml methanol to produce a clear solution. This is heated to 40° C. for 30 minutes during which a precipitate forms. The result is stirred over night, the product is filtered off and washed with water. Yield: 0.8 g (61%) pale brown crystals Melting point: 184° C.

4) 2-[2,4-Dichloro-5-(2-propynyloxy)phenyl]-5,6,7,8-tetrahydro-1,2,4-triazolo[4,3-a]pyridine-3(2H)-one N-Chlorocarbonyl-2-chloro-1,4,5,6-tetrahydro-pyridine (4.32 g, 0.024 mol) dissolved in 20 ml acetonitrile are added to a stirred suspension of formic acid N'-(2,4-dichloro-5-(2-propinyloxy)-phenyl) hydrazide (5.18 g, 0.02 mol) in 250 ml acetonitrile at 0°–10° C. for 20 minutes. This is then reacted at the same temperature with triethylamine (4.04 g, 0.04 mol) and dissolved in 20 ml acetonitrile. This is stirred for one hour at 5°–10° C. and a colourless precipitate precipitates out. This is heated for 4 hours to 50°–55° C. and then stirred for one night at room temperature. The batch is reacted with 30 ml 6N hydrochloric acid and stirred for 1 hour at 50° C. The solvent is drawn off under reduced pressure and the residue digested with iced water. The resultant pale grey precipitate is separated by filtration, washed with water and dried at 50°–60° C. Yield: 6.6 g (=97.6%) Melting point: 160°–162° C.

We claim:

1. A process for the preparation of compounds of type (I),

(I)

wherein

X=O or S, $R^1$=($C_2$–$C_8$) alkoxyalkyl, ($C_2$–$C_8$) haloalkoxyalkyl, ($C_1$–$C_8$) alkyl, ($C_1$–$C_8$) haloalkyl, ($C_1$–$C_8$) cyanoalkyl, ($C_2$–$C_8$) alkylthioalkyl, ($C_2$–$C_8$) alkylsulfinylalkyl, ($C_2$–$C_8$) alkylsulfonylalkyl, ($C_7$–$C_8$) arylalkyl, ($C_2$–$C_8$) alkenyl, ($C_2$–$C_8$) haloalkenyl, ($C_2$–$C_8$) alkinyl, ($C_2$–$C_8$) haloalkinyl, aryl, that may be substituted one or more times with halogen, ($C_1$–$C_3$) alkyl or ($C_1$–$C_3$) alkoxy, heteroaryl, where heteroaryl may optionally be substituted by halogen, $R^2$ and $R^3$, independently of one another represent, H, ($C_2$–$C_6$) alkoxyalkyl, ($C_2$–$C_6$) haloalkoxyalkyl, ($C_1$–$C_6$) alkyl, ($C_1$–$C_6$) haloalkyl, ($C_1$–$C_6$) cyanoalkyl, ($C_1$–$C_6$) alkylthio, ($C_2$–$C_6$) alkylthioalkyl, ($C_2$–$C_6$) alkylsulfinylalkyl, ($C_2$–$C_6$) alkylsulfonylalkyl, ($C_7$–$C_8$) arylalkyl, ($C_2$–$C_6$) alkenyl, ($C_2$–$C_6$) haloalkenyl, ($C_2$–$C_6$) alkinyl, ($C_2$–$C_6$) haloalkinyl, aryl, that may be substituted one or more times with halogen, ($C_1$–$C_3$) alkyl or ($C_1$–$C_3$) alkoxy, heteroaryl, where $R^1$ and $R^2$ may also be associated to form a ring to produce structure (II),

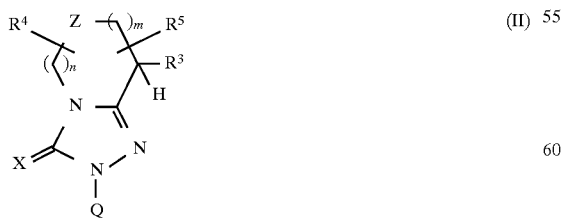
(II)

wherein n and m independently of one another are 0, 1, 2 or 3,

Z=$CR^4R^5$, O, S, S(O), S(O)$_2$, N(($C_1$–$C_4$)alkyl), N(($C_1$–$C_4$)haloalkyl), C=O, C=N—$R^4$ or C=S, $R^4$=H, ($C_1$–$C_3$) alkyl, halogen, ($C_1$–$C_6$) alkoxy, ($C_1$–$C_6$) haloalkyl, ($C_1$–$C_6$) haloalkoxy, ($C_2$–$C_6$) alkylcarbonyloxy or ($C_2$–$C_6$) haloalkylcarbonyloxy, $R^5$=H, ($C_1$–$C_3$) alkyl or halogen, where $R^4$ and $R^5$, independently of one another, can substitute the ring one or more times and occupy up to 12 (m=3, n=3) positions, Q stands for one of the radicals

Q-1

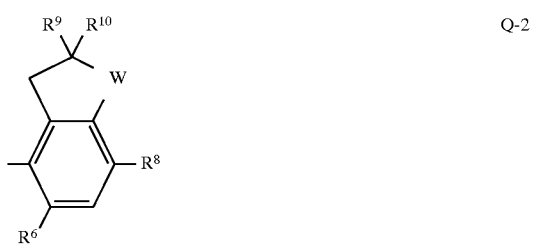
Q-2

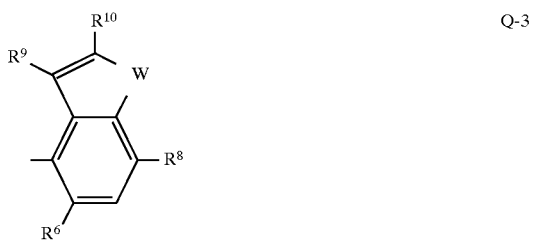
Q-3

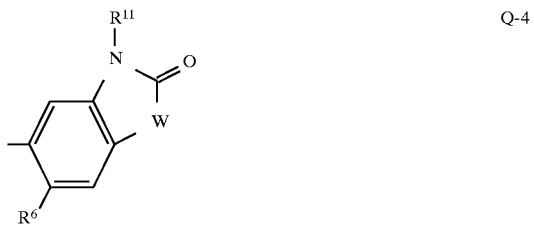
Q-4

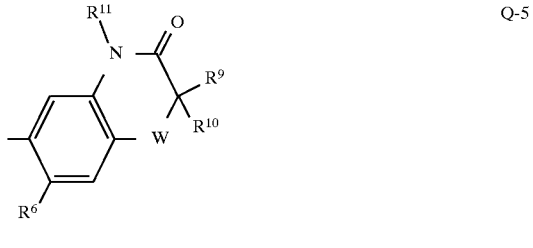
Q-5

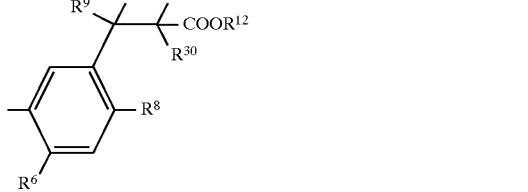
Q-6

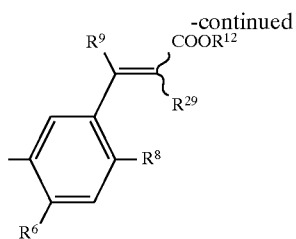

Q-7 wherein

W=O or S, $R^6$=H, halogen, $R^7$=H, $(C_1-C_8)$ alkyl, $(C_1-C_8)$ haloalkyl, halogen, OH, $OR^{12}$, SH, $S(O)_pR^{12}$, $COR^{12}$, $CO_2R^{12}$, $C(O)SR^{12}$, $C(O)NR^{14}R^{15}$, CHO, $CR^{14}$=$NOR^{21}$, $CHCR^{22}CO_2R^{12}$, $CH_2CHR^{22}CO_2R^{12}$, $CO_2N$=$CR^{16}R^{17}$, $NO_2$, CN, $NHSO_2R^{18}$, $NHSO_2NHR^{18}$, $NR^{12}R^{23}$, $NH_2$ or phenyl, optionally substituted by $R^{24}$, p=0,1 or 2, $R^8$=$(C_1-C_2)$ alkyl, $(C_1-C_2)$ haloalkyl, $OCH_3$, $SCH_3$, $OCHF_2$, halogen, CN or $NO_2$, $R^9$=H, $(C_1-C_3)$ alkyl or halogen, $R^{10}$=H, $(C_1-C_3)$ alkyl, halogen, $(C_1-C_3)$ haloalkyl, cyclopropyl, Vinyl, $(C_2-C_8)$ alkinyl, CN, $C(O)R^{23}$, $CO_2R^{23}$, $C(O)NR^{23}R^{25}$, $CR^{19}R^{20}CN$, $CR^{19}R^{20}C(O)R^{23}$, $CR^{19}R^{20}CO_2R^{23}$, $CR^{19}R^{20}C(O)NR^{23}R^{25}$, $CHR^{19}OH$, $CHR^{19}OC(O)R^{23}$ or $OCHR^{19}OC(O)NR^{23}R^{25}$, or, when Q equals Q-2, $R^9$ and $R^{10}$ can together with the carbon atom to which they are bound be C=O, $R^{11}$=H, $(C_1-C_6)$ alkyl, $(C_1-C_6)$ haloalkyl, $(C_3-C_6)$ haloalkenyl, $(C_2-C_6)$ alkoxyalkyl, $(C_3-C_6)$ alkenyl, $(C_3-C_6)$ alkinyl, $(C_3-C_6)$ haloalkinyl, $(C_4-C_7)$ cycloalkylalkyl,

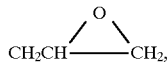

$R^{12}$=$(C_1-C_8)$ alkyl, $(C_3-C_8)$ cycloalkyl, $(C_3-C_8)$ alkenyl, $(C_3-C_8)$ alkinyl, $(C_1-C_8)$ haloalkyl, $(C_2-C_8)$ alkoxyalkyl, $(C_2-C_8)$ alkylthioalkyl, $(C_2-C_8)$ alkylsulfinylalkyl, $(C_2-C_8)$ alkylsulfonylalkyl, $(C_4-C_8)$ alkoxyalkoxyalkyl, $(C_4-C_8)$ cycloalkylalkyl, $(C_6-C_8)$ cycloalkoxyalkyl, $(C_4-C_8)$ alkenyloxyalkyl, $(C_4-C_8)$ alkinyloxyalkyl, $(C_3-C_8)$ haloalkoxyalkyl, $(C_4-C_8)$ haloalkenyloxyalkyl, $(C_4-C_8)$ haloalkinyloxyalkyl, $(C_6-C_8)$ cycloalkylthioalkyl, $(C_4-C_8)$ alkenylthioalkyl, $(C_4-C_8)$ alkinylthioalkyl, $(C_1-C_4)$ alkyl, substituted by phenoxy or benzyloxy, each ring optionally substituted by halogen, $(C_1-C_3)$ alkyl or $(C_1-C_3)$ haloalkyl, $(C_4-C_8)$ trialkylsilylalkyl, $(C_3-C_8)$ cyanoalkyl, $(C_3-C_8)$ halocycloalkyl, $(C_3-C_8)$ haloalkenyl, $(C_5-C_8)$ alkoxyalkenyl, $(C_5-C_8)$ haloalkoxyalkenyl, $(C_5-C_8)$ alkylthioalkenyl, $(C_3-C_8)$ haloalkinyl, $(C_5-C_8)$ alkoxyalkinyl, $(C_5-C_8)$ haloalkoxyalkinyl, $(C_5-C_8)$ alkylthioalkinyl, $(C_2-C_8)$ alkylcarbonyl, benzyl, optionally substituted by halogen, $(C_1-C_3)$ alkyl or $(C_1-C_3)$ haloalkyl, $CHR^{19}COR^{13}$, $CHR^{19}P(O)(OR^{13})_2$, $CHR^{19}P(S)(OR^{13})_2$, $P(O)(OR^{13})_2$, $P(S)(OR^{13})_2$, $CHR^{19}C(O)NR^{14}R^{15}$, $CHR^{19}C(O)NH_2$, $CHR^{19}CO_2R^{13}$, $CO_2R^{13}$, $SO_2R^{13}$, phenyl, optionally substituted by $R^{24}$,

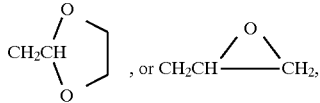

$R^{13}$=$(C_1-C_6)$ alkyl, $(C_1-C_6)$ haloalkyl, $(C_3-C_6)$ alkenyl or $(C_3-C_6)$ alkinyl, $R^{14}$ and $R^{16}$=independently of one another, H or $(C_1-C_4)$ alkyl, $R^{15}$ and $R^{17}$=independently of one another, $(C_1-C_4)$ alkyl or phenyl, optionally substituted by halogen, $(C_1-C_3)$ alkyl or $(C_1-C_3)$ haloalkyl, or $R^{14}$ and $R^{15}$ can, together with the nitrogen atom that binds them, form a piperidinyl-, pyrrolidinyl- or morpholinyl-ring, each ring optionally substituted by $(C_1-C_3)$ alkyl, phenyl or benzyl, or $R^{16}$ and $R^{17}$ can, together with the carbon atom that binds them, be $(C_3-C_8)$ cycloalkyl, $R^{18}$=$(C_1-C_4)$ alkyl or $(C_1-C_4)$ haloalkyl, $R^{19}$ and $R^{20}$=independently H or $(C_1-C_5)$ alkyl, $R^{21}$=H, $(C_1-C_6)$ alkyl, $(C_3-C_6)$ alkenyl or $(C_3-C_6)$ alkinyl, $R^{22}$ and $R^{27}$=independently of one another, H, $(C_1-C_4)$ alkyl or halogen, or $R^{12}$ and $R^{22}$ can together form a $(C_2-C_3)$ alkylen, $R^{23}$, $R^{24}$ and $R^{28}$=independently of one another, H or $(C_1-C_4)$ alkyl, $R^{25}$=$(C_1-C_2)$ alkyl, $(C_1-C_2)$ haloalkyl, $OCH_3$, $SCH_3$, $OCHF_2$, halogen, CN or $NO_2$ and $R^{26}$=H, $(C_1-C_5)$ alkyl, $(C_{1-C5})$ haloalkyl, $(C_3-C_6)$ cycloalkyl, $(C_3-C_6)$ halocycloalkyl, $(C_1-C_5)$ alkoxy, $(C_{1-C5})$ haloalkoxy and phenyl, that may optionally be substituted up to three times optionally by halogen, $NO_2$, cyano, $(C_1-C_2)$ alkyl, $(C_1-C_2)$ haloalkyl, $(C_1-C_2)$ alkoxy or $(C_1-C_2)$ haloalkoxy, $R^{29}$=H, halogen or $(C_1-C_6)$ alkyl, $R^{30}$=H, $(C_1-C_4)$ alkyl or halogen, wherein amides of formula (IV)

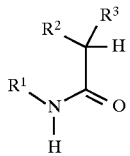
(IV)

wherein $R^1$, $R^2$ and $R^3$ have the meaning given above are reacted with phosgen or thiophosgen or a phosgen substitute or thiophosgen substitute optionally in a solvent to a compound of formula (V)

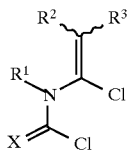
(V)

wherein $R^1$, $R^2$ and $R^3$ and X have the meaning given above and these compounds of formula (V) are then reacted with a compound of formula (VI) or an acid addition salt thereof,

(VI)

wherein Q and $R^{226}$ have the meaning given above optionally in the presence of a diluting agent and optionally initially in the presence of a base and then in the presence of an acid and optionally by increasing the temperature to a compound of formulae (I) or (II).

2. The process of claim 1, wherein the synthesis sequences occur in a reaction vessel starting from the compounds of formulae (X) and (XI) without intermediate isolation.

3. The process of claim 1, wherein the cited synthesis sequence occurs without changing the solvent.

4. The process of claim 1, wherein organic or inorganic acids selected from HCl, $H_2SO_4$, $HNO_3$, $HCO_2H$, p-toluene sulfonic acid, acetic acid, camphorsulfonic acid or $H_3PO_4$ or an acid ion exchanger are used as the acid.

5. The process of claim 4, wherein hydrochloric acid, sulfuric acid or phosphoric acid is used as the acid.

6. The process of claim 1, wherein the reaction sequence is carried out at a temperature between $-20°$ C. and $120°$ C.

7. The process of claim 1, wherein acetic acid ethyl ester or acetonitrile or mixtures of the two are used as the solvent.

8. The process of claim 1, wherein an organic base, an inorganic base or an alcoholate is used as the base.

9. The process of claim 8, wherein triethylamine, tributylamine, pyridine, tetramethylpiperidine, NaOH, KOH, $Ca(OH)_2$, $Na_2CO_3$, $K_2CO_3$, $CaCO_3$, $NaHCO_3$, $KHCO_3$, $NaOCH_3$ or $NaOC_2H_5$ is used as the base.

10. The process of claim 9, wherein $K_2CO_3$, $Na_2CO_3$, triethylamine or tributylamine is used as the base.

11. A process of claim 1, wherein the reaction sequence is carried out at a temperature between $-20°$ C. and $80°$ C.

12. The process of claim 1, wherein $R^1$ is a benzyl.

13. The process of claim 1, wherein $R^1$ is a naphthyl or phenyl.

14. The process of claim 1, wherein $R^1$ is a pyridine.

15. The process of claim 1, wherein $R^2$ and/or $R^3$ are a benzyl.

16. The process of claim 1, wherein $R^2$ and/or $R^3$ are a naphthyl or phenyl.

17. The process of claim 1, wherein $R^2$ and/or $R^3$ are a pyridine.

* * * * *